United States Patent [19]

de La Poterie et al.

[11] Patent Number: 5,672,647
[45] Date of Patent: Sep. 30, 1997

US005672647A

[54] AQUEOUS NAIL VARNISH CONTAINING A FILM-FORMING POLYMERIC DISPERSION AND A PERFLUOROALKYL COMPOUND

[75] Inventors: Valerie de La Poterie, Rungis; Myriam Mellul, L'Hay les Roses, both of France

[73] Assignee: L'Oreal, Paris, France

[21] Appl. No.: 455,905

[22] Filed: May 31, 1995

Related U.S. Application Data

[63] Continuation-in-part of Ser. No. 248,877, May 25, 1994, Pat. No. 5,571,858.

[30] Foreign Application Priority Data

May 26, 1993 [FR] France ................... 93 06329

[51] Int. Cl.$^6$ ........................................... C08K 5/02
[52] U.S. Cl. ................... 524/463; 524/462; 524/589; 524/590; 524/556; 524/577; 427/372; 427/374.1; 427/384
[58] Field of Search ................... 524/462, 463, 524/589, 590, 556, 577; 427/372.2, 374.1, 384

[56] References Cited

U.S. PATENT DOCUMENTS 5,264,242  11/1993  Speer ........................ 427/140

FOREIGN PATENT DOCUMENTS

| 0558423 | 9/1993 | European Pat. Off. . |
|---|---|---|
| 2677982 | 12/1992 | France . |
| 1032367 | 6/1966 | United Kingdom . |
| 1074201 | 6/1967 | United Kingdom . |
| 8806434 | 9/1988 | WIPO . |
| 9311103 | 6/1993 | WIPO . |

*Primary Examiner*—Paul J. Thibodeau
*Assistant Examiner*—Mary Critharis
*Attorney, Agent, or Firm*—Cushman Darby & Cushman IP Group of Pillsbury Madison & Sutro LLP

[57] ABSTRACT

An aqueous nail varnish free from nitrocellulose and having improved spreading properties contains 10 to 59 weight percent of a film-forming polymer present in a dispersed state, 0.01 to 1 weight percent of a water-soluble perfluoroalkyl and 40 to 90 weight percent of water.

10 Claims, No Drawings

AQUEOUS NAIL VARNISH CONTAINING A FILM-FORMING POLYMERIC DISPERSION AND A PERFLUOROALKYL COMPOUND

This application is a continuation-in-part of application Ser. No. 08/248,877, filed May 25, 1994, now U.S. Pat. No. 5,571,858 the entire contents of which is herein incorporated by reference.

FIELD OF THE INVENTION

The present invention relates to a cosmetic composition in the form of a colored or colorless aqueous nail varnish, free from nitrocellulose, containing a film-forming polymer in the dispersed state and at least one water-soluble organic compound of the perfluoroalkyl type.

BACKGROUND OF THE INVENTION

At the present time most compositions which are in the form of nail varnishes are based on a mixture of organic solvents containing nitrocellulose, an arylsulphonamide-formaldehyde resin or an alkyd resin and a plasticizing agent. Because of the presence of organic solvents, such varnishes have a number of disadvantages insofar as they can damage the nails or the cuticle and, furthermore, cause some hazard to female users during application and drying.

In order to prevent such disadvantages, there has been disclosed in U.S. Pat. No. 5,284,885 nail coatings containing an aqueous nitrocellulose having a high percentage of water but still containing a substantial amount of an organic solvent.

However, in addition to the consequences of using organic solvents, nitrocellulose has also some drawbacks, namely poor gloss and a tendency to shrink and to become brittle. Further, such hazards, attendant on nitrocellulose, are not to be neglected.

Research has therefore been aimed for a number of years to the development of aqueous nail varnishes free from organic solvents and nitrocellulose as a film forming substance.

While some results have been successfully obtained with some aqueous nail varnishes, it was found that the presence of a high proportion of water resulted not only in a mediocre spreading of the varnish on the surface of the nails, but also in the formation of pits or shrinkage of the varnish.

The problem of varnish spreading is actually crucial for uniform application and good coating of the nail surface.

This problem is closely related to the surface tension of the nail varnish composition, which must be as low as possible so as to obtain good varnish spreading on the nail.

It is well known from the state of the art that surface-active agents can lower surface tension of aqueous compositions. Nevertheless, it has been found that in the case of aqueous nail varnishes all surfactants could not contribute this property.

SUMMARY OF THE INVENTION

After many investigations into a large number of surface-active agents, it was found possible to significantly improve the spreading properties of aqueous nail varnishes by employing, as surface-active agents, water-soluble organic compounds of the perfluoroalkyl type. The use of such compounds was found, in fact, to be clearly superior to the use of silicone type surface-active agents which surface-active type agents are known to improve spreading.

The presence of at least one perfluoroalkyl compound in aqueous nail varnish compositions free from organic solvent, has the effect of considerably modifying spreading characteristics without, however, modifying the intrinsic properties of the varnish.

DETAILED DESCRIPTION

The present invention is, therefore, a novel industrial product which is a colorless, aqueous nail varnish free from nitrocellulose and additionally containing (a) 10 to 59 percent by weight of a film-forming polymer present in a dispersed state, (b) 0.01 to 1 percent by weight of a water-soluble perfluoroalkyl having the formula, $$(C_nF_{2n+1})-R_1 \qquad (I)$$

wherein $C_nF_{2n+1}$ is linear or branched and n ranges from 4 to 16, and $R_1$ is a residue selected from the group consisting of:

(i) $-SO_3^{\ominus}NH_4^{\oplus}$, (ii) $-SO_3^{\ominus}N^{\oplus}(R_3)_4$, wherein $R_3$ is $C_1-C_4$ alkyl, (iii) $-CO_2^{\ominus}NH_4^{\oplus}$, (iv) $-CO_2^{\ominus}N^{\oplus}(R_3)_4$, wherein $R_3$ has the meaning given above, (v) $-SO_2N(R_3)CH_2-CO_{22}^{\ominus}X^{\oplus}$, wherein $R_3$ has the meaning given above and X represents hydrogen or an alkali metal, (vi) $-SO_2NH(CH_2)_pN^{\oplus}(R_3)_3I^{\ominus}$, wherein p represents 1, 2, 3 or 4 and $R_3$ has the meaning given above, and (vii) $-SO_2N(R_3)(CH_2CH_2O)-Y$, wherein Y represents hydrogen or $C_1-C_4$ alkyl, and $R_3$ has the meaning above, and (c) 40 to 90 percent by weight of water, the amounts of components (a), (b) and (c) being based on the total weight of said nail varnish.

Particularly representative perfluoroalkyl compounds of formula (I) comprise compounds having the formula (a) $C_nF_{2n+1}SO_2N(C_2H_5)CH_2CO_2^{\ominus}K^{\oplus}$, wherein n equals 8, and is sold under the name of "FLUORAD FC 129®" by 3M;

(b) $C_nF_{2n+1}SO_2NHC_3H_6N^{\oplus}(CH_3)_3I^{\ominus}$, wherein n equals 8, and is sold under the name of "FLUORAD FC 135®" by 3M;

(c) $C_nF_{2n+1}SO_2N(C_2H_5)(CH_2CH_2O)-H$, wherein n equals 8, and is sold under the name of "FLUORAD FC 170C®" by 3M;

(d) $C_nF_{2n+1}SO_3^{\ominus}NH_4^{\oplus}$, wherein n equals 10, and is sold under the name of "FLUORAD FC 120®" by 3M; and (e) $C_nF_{2n+1}SO_2N(C_2H_5)CH_2CO_2^{\ominus}NH_4^{\oplus}$, wherein n equals 8, and is sold under the name of "FLUORAD FC 143®" by 3M.

The particularly preferred content of such perfluoroalkyl compounds of formula (I) generally ranges from 0.05 to 0.2 percent by weight relative to the total weight of said nail varnish.

The said film-forming polymer which is preferably employed in the aqueous dispersed state, forms the following preferred dispersions:

(A) dispersions of anionic, cationic or nonionic polyurethane and dispersions of polyurethane copolymers; among such dispersions are those particularly mentioned in Patents EP-143, 480 and 391,322 and in particular those sold by ICI under the names of: "NEOREZ-R974®" and "NEOPAC E106®", and that sold by Witco Co. under the name "WITCOBOND 231®", and (B) dispersions of acrylic, styrenic, vinylic and styrenic-acrylic polymers and copolymers;

among such dispersions are those particularly mentioned in Japanese Patent Applications JP-04-103,511, JP-04-103,512, JP-04-103,513, JP-04-03,514, JP-04-103,515, JP-04-103,516, JP-54-52,736, JP-55-70,209 and JP-02-221,214; in French Patents FR-1,559,020, FR-2,399,238 and FR-2,537,871; in U.S. Pat. No. 4,126,144 and 4,166,913; in Patent EP-140,325, in Patent DE-3,931,237 and in Patent CA-1,225,035, and in particular those sold by ICI under the names of "NEOCRYL-XK53®", "NEOCRYL-XK90®" and "NEOCRYL-XK62®" and that of Rhone-Poulenc disclosed as "RHODOPASS G5125®".

According to the present invention the said aqueous nail varnishes may contain various cosmetic ingredients and especially organic and inorganic pigments.

Representative organic pigments include, for instance, D&C Reds Nos. 10, 11, 12 and 13, D&C Red No. 7, D&C Reds Nos. 5 and 6, D&C Reds Nos. 30 and 34, lacquers such as D&C Yellow No. 5 lacquer and D&C Red No. 2 lacquer. Guanine may also be mentioned.

Representative inorganic pigments include, for instance, titanium dioxide, bismuth oxychloride, brown iron oxide and red iron oxides.

Generally, such pigments are present in an amount ranging from 0.05 to 5 percent by weight relative to the total weight of said nitrocellulose free nail varnish.

Furthermore, to prevent such pigments from settling, the nail varnish composition of the present invention can contain an effective amount of clay, a hydrated calcium silicate or a magnesium silicate.

Representative other components of the nail varnish according to the present invention include a preserving agent, a perfume, a plasticizer, an auxiliary film-forming substance, a thickener, a hydrating agent, an anti-foam component, a wax, a drying accelerator, a UV filter, as well as a small proportion of other surface-active agents, such as those of the silicone type.

The following aqueous, nitrocellulose free nail varnishes, illustrate the present invention.

Further, the letters "AS" mean "Active Substance", that is to say, in this case, the film-forming polymer is present, as a specific percent in the particularly disclosed nail varnish composition.

EXAMPLE 1

Colored Nail Varnish

| | |
|---|---|
| Polyurethane dispersion (40 percent in water), sold by ICI under the name of "NEOREZ R974 ® " | 95% (384 AS) |
| Pigments | 1.5% |
| Perfluoroalkyl compound, sold under the name of "FLUORAD FC143 ® " | 0.2% |
| Thickener of the polyurethane type sold by Akzo under the name of "DAPRAL T210 ® " | 0.3% |
| Water, q.s. | 100% |

Example 2: Colored nail varnish

| | |
|---|---|
| Polyurethane dispersion (40% in water), sold by ICI under the name of "NEOREZ R974 ® " | 50% (204 AS) |
| Pigments | 1.5% |
| Perfluoroalkyl compound, sold under the name of "FLUORAD FC143 ® " | 0.1% |
| Thickener of the polyurethane type, sold by Akzo under the name of "DAPRAL T210 ® " | 0.5% |
| Water, q.s. | 100% |

Example 3: Colored nail varnish

| | |
|---|---|
| Polyurethane dispersion (30 percent in water) sold by Witco under the name of "WITCOBOND 231 ® " | 90% (27% AS) |
| Pigments | 1.5% |
| Perfluoroalkyl compound, sold under the name of "FLUORAD FC143 ® " | 0.2% |
| Thickener of the polyurethane type, sold by Akzo under the name of "DAPRAL T210 ® " | 0.3% |
| Water, q.s. | 100% |

Example 4: Colored nail varnish

| | |
|---|---|
| Polyacrylic dispersion (45 percent in water) sold by ICI under the name "NEOCRYL XK90 ® " | 60% (274 AS) |
| Pigments | 1.5% |
| Perfluoroalkyl compound, sold under the name of "FLUORAD FC143 ® " | 0.2% |
| Thickener of the polyurethane type, sold by Akzo under the name of "DAPRAL T210 ® " | 0.3% |
| Water, q.s. | 100% |

COMPARATIVE EXAMPLES OF NAIL VARNISHES

Example A:

| | |
|---|---|
| Polyurethane dispersion (40 percent in water), sold by ICI under the name of "NEOREZ R974 ® " | 95% (38% AS) |
| Pigments | 1.5% |
| Thickener of the polyurethane type, sold by Akzo under the name of "DAPRAL T210 ® " | 0.3% |
| Water, q.s. | 100%] |

Example B:

| | |
|---|---|
| Polyurethane dispersion (40 percent in water), sold by ICI under the name "NEOREZ R974 ® " | 95% (38% AS) |
| Pigments | 1.5% |
| Silicone surfactant, sold by Shin Etsu under the name of "KF 355A ® " | 0.2% |
| Thickener of the polyurethane type, sold by Akzo under the name of "DAPRAL T210 ® " | 0.3% |
| Water, q.s. | 100% |

Example C:

| | |
|---|---|
| Polyurethane dispersion (40 percent in water), sold by ICI under the name of "NEOREZ R974 ® " | 95% (38% AS) |
| Pigments | 1.5% |
| Silicone surfactant, sold by Shin Etsu under the name of "KF 355A ® " | 0.1% |
| Thickener of the polyurethane type, sold by Akzo under the name of "DAPRAL T210 ® " | 0.3% |
| Water, q.s. | 100% |

The nail varnishes of Examples 1 and 2 spread regularly and uniformly. A single application of a nail varnish suffices to obtain a regular coat and a smooth film.

The nail varnishes of comparative Examples A to C, which do not contain a water-soluble perfluoroalkyl compound of formula (I) or which contain a silicone compound instead, do not spread uniformly and regularly. The resulting film is non homogeneous and the aqueous nail varnish must be applied several times to obtain a regular coat.

We claim:

1. A colored aqueous nail varnish free from nitrocellulose and having spreading properties on the nail, said aqueous nail varnish consisting of:

(a) 10 to 59 percent by weight of a film-forming polymer present in a dispersed state, (b) 0.01 to 1 percent by weight of a water-soluble perfluoroalkyl having the formula:

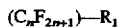 (I)

wherein $C_nF_{2n+1}$ is linear or branched and n ranges from 4 to 16, and $R_1$ is a residue selected from the group consisting of:
(i) $-SO_3^{\ominus}NH_4^{\oplus}$,
(ii) $-SO_3^{\ominus}N^{\oplus}(R_3)_4$, wherein $R_3$ is $C_1-C_4$ alkyl,
(iii) $-CO_2^{\ominus}NH_4^{\oplus}$,
(iv) $-CO_2^{\ominus}N^{\oplus}(R_3)_4$, wherein $R_3$ has the meaning given above,
(v) $-SO_2N(R_3)CH_2-CO_2^{\ominus}X^{\oplus}$, wherein $R_3$ has the meaning given above and X represents hydrogen or an alkali metal,
(vi) $-SO_2NH(CH_2)_pN^{\oplus}(R_{33}I^{\ominus}$, wherein p represents 1, 2, 3 or 4 and $R_3$ has the meaning given above, and
(vii) $-SO_2N(R_3)(CH_2CH_2O)-Y$, wherein Y represents hydrogen or $C_1-C_4$ alkyl, and $R_3$ has the meaning above, (c) 40 to 90 percent by weight of water,
(d) 0.05 to 5 percent by weight of an organic or inorganic pigment, and
(e) a cosmetic ingredient selected from the group consisting of a preserving agent, a perfume, a plasticizer, an auxiliary film-forming substance, a thickener, a hydrating agent, a wax, a drying accelerator, a UV filter, a silicone surface-active agent and a mixture thereof, the amounts of components (a), (b), (c) and (d) being based on the total weight of said nail varnish.

2. A colored aqueous nail varnish free from nitrocellulose and having spreading properties on the nail, said aqueous nail varnish consisting of:
(a) 10 to 59 percent by weight of a film-forming polymer present in a dispersed state,
(b) 0.01 to 1 percent by weight of a water-soluble perfluoroalkyl having the formula:

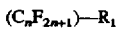 (I)

wherein $C_nF_{2n+1}$ is linear or branched and n ranges from 4 to 16, and $R_1$ is a residue selected from the group consisting of:
(i) $-CO_2^{\ominus}NH_4^{\oplus}$,
(ii) $-CO_2^{\ominus}N^{\oplus}(R_3)_4$, wherein $R_3$ has the meaning given above,
(iii) $-SO_2N(R_3)CH_2-CO_2^{\ominus}X^{\oplus}$, wherein $R_3$ has the meaning given above and X represents hydrogen or an alkali metal, (iv) $-SO_2NH(CH_2)_pN^{\oplus}(R_3)_3I^{\ominus}$, wherein p represents 1, 2, 3 or 4 and $R_3$ has the meaning given above, and
(v) $-SO_2N(R_3)(CH_2CH_2O)-Y$, wherein Y represents hydrogen or $C_1-C_4$ alkyl, and $R_3$ has the meaning above, (c) 40 to 90 percent by weight of water,
(d) 0.05 to 5 percent by weight of an organic or inorganic pigment, and
(e) a cosmetic ingredient selected from the group consisting of a preserving agent, a perfume, a plasticizer, an auxiliary film-forming substance, a thickener, a hydrating agent, a wax, a drying accelerator, a UV filter, a silicone surface-active agent and a mixture thereof, the amounts of components (a), (b), (c) and (d) being based on the total weight of said nail varnish.

3. The nail varnish of claim 1 wherein said water-soluble perfluoroalkyl of formula (I) is present in an amount ranging from 0.05 to 0.2 percent by weight relative to the total weight of said nail varnish.

4. The nail varnish of claim 1 wherein said film-forming polymer is selected from the group consisting of an anionic polyurethane, a cationic polyurethane, a nonionic polyurethane, a cationic polyurethane, a nonionic polyurethane, a polyurethane copolymer, an acrylic polymer, a styrenic polymer, a vinylic polymer, a styrenic-acrylic polymer, an acrylic copolymer, a styrenic copolymer, a vinylic copolymer and a styrenic-acrylic copolymer.

5. The nail varnish of claim 1 wherein said organic or inorganic pigment is present in an amount ranging from 0.05 to 5 percent by weight relative to the total weight of said nail varnish.

6. A method of coating a nail of a person comprising applying the varnish of claim 1 to said nail and allowing said varnish to dry.

7. A method of coating a nail of a person comprising applying the varnish of claim 2 to said nail and allowing said varnish to dry.

8. A method of coating a nail of a person comprising applying the varnish of claim 3 to said nail and allowing said varnish to dry.

9. A method of coating a nail of a person comprising applying the varnish of claim 2 to said nail and allowing said varnish to dry.

10. A method of coating a nail of a person comprising applying the varnish of claim 5 to said nail and allowing said varnish to dry.

* * * * *